United States Patent [19]

Fredeking

[11] Patent Number: 4,678,458

[45] Date of Patent: Jul. 7, 1987

[54] METHOD FOR AVOIDING MISTAKES DURING PLASMAPHERESIS

[76] Inventor: Terry M. Fredeking, 7520 David Dr., Fort Worth, Tex. 76118

[21] Appl. No.: 872,030

[22] Filed: Jun. 9, 1986

[51] Int. Cl.⁴ .............................................. A61M 5/00
[52] U.S. Cl. ...................................... 604/6; 604/111; 604/189; 604/404
[58] Field of Search .................... 128/771; 604/6, 110, 604/111, 189, 408–410, 404

[56] References Cited

U.S. PATENT DOCUMENTS

| | | | |
|---|---|---|---|
| 2,894,510 | 7/1959 | Bellamy | 604/408 |
| 3,072,120 | 1/1963 | Sharp et al. | 604/189 |
| 3,523,522 | 8/1970 | Whitehead et al. | 128/771 |
| 3,625,212 | 12/1971 | Rosenberg et al. | 604/6 |
| 3,831,625 | 8/1974 | Roediger | 604/111 X |
| 4,150,673 | 4/1979 | Watt | 604/110 X |
| 4,195,631 | 4/1980 | Baucom . | |
| 4,256,132 | 3/1981 | Gunter | 604/189 X |
| 4,365,629 | 12/1982 | Pert et al. | 604/408 |
| 4,425,113 | 1/1984 | Bilstad . | |

*Primary Examiner*—Dalton L. Truluck
*Attorney, Agent, or Firm*—Charles D. Gunter

[57] ABSTRACT

An apparatus and method are shown for eliminating mistakes during plasmapheresis procedures in returning red blood cells to a correct donor. In the procedure, a portion of the return blood flow line is rendered inoperative by a lock device. A key, unique to the donor, is attached to the blood collection bag prior to the centrifuging operation which separates the blood into plasma and red blood cells. After the centrifuge operation, flow between the collection bag and the donor can only be established by utilizing the unique key in the correct lock box.

13 Claims, 8 Drawing Figures

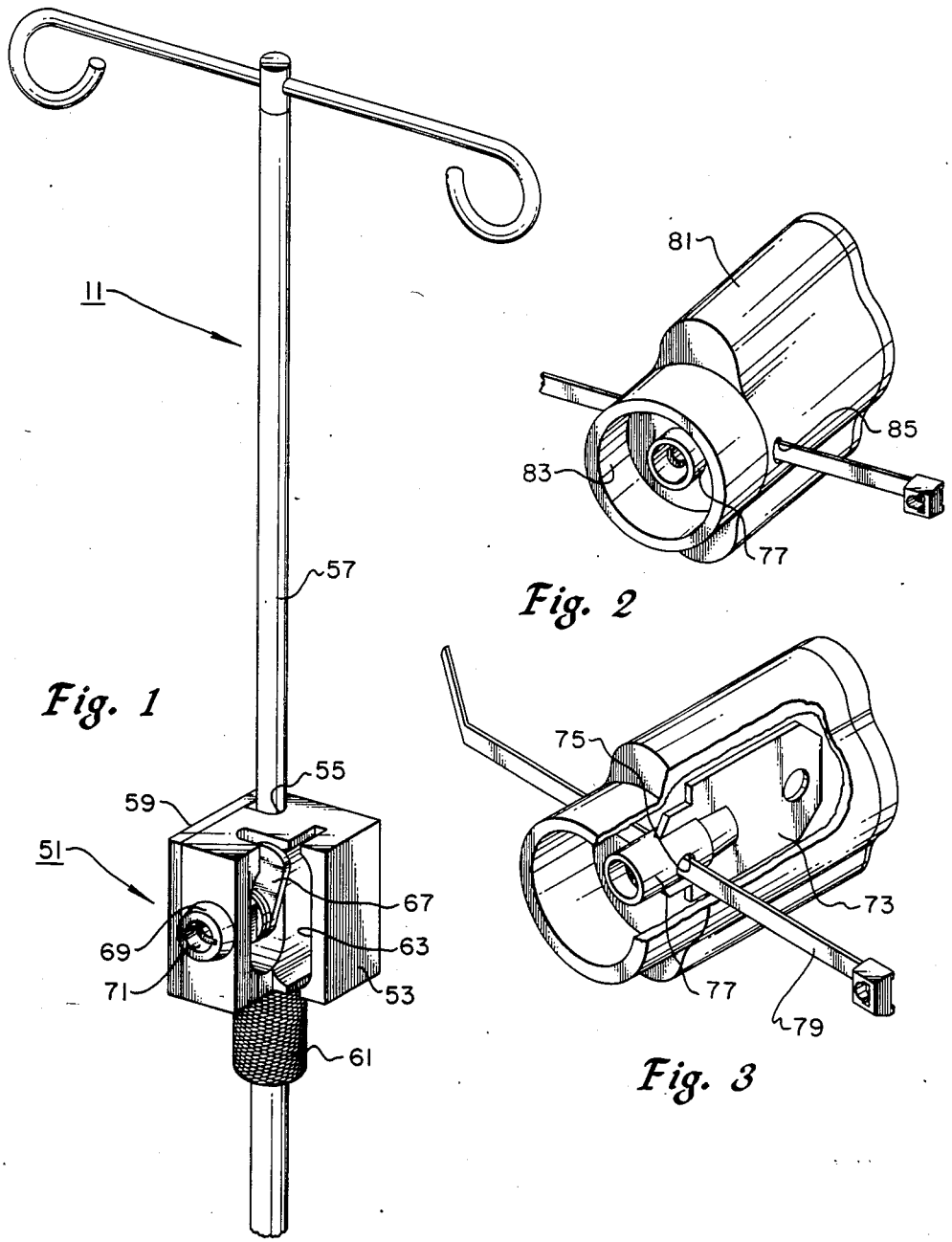

METHOD FOR AVOIDING MISTAKES DURING PLASMAPHERESIS

BACKGROUND OF THE INVENTION

1. Field of the Invention

The present invention relates to plasmapheresis apparatus and processes and, specifically, to safety procedures for matching blood donors with returned blood components.

2. Description of the Prior Art

Plasmapheresis is a process for obtaining plasma from a blood donor by extracting blood, centrifuging the blood to remove plasma, and then returning red blood cells to the donor. The critical danger in plasmapheresis procedures is that the red blood cells might be inadvertently returned to the wrong donor. This type mistake results in serious health complications and can even result in death of the blood donor.

The prior art techniques used to insure safety in plasmapheresis procedures have included visual matching of identifying indicia on the blood collection bag with and the donor, the donor's cot number, or the like. The indicia used in an attempt to correctly match the blood collection bag with the correct donor have included color matching, numerical data, as well as the matching of distinctive plugs and receptacles associated with the blood collection bag and blood donor.

The present invention has as its object an improved method for avoiding mistakes in returning red blood cells to the correct donor during plasmapheresis by rendering the blood return system inoperative until identifying indicia have been verified.

Another object of the plasmapheresis method of the invention is to seal the reinfusion port of the blood collection container until such time as the identifying indicia on the bag have been matched with the correct donor.

Another object of the invention is the provision of an apparatus for rendering the return blood system inoperative which utilizes a lock box which must be operated by a unique key which forms a part of the identifying indicia associated with the blood collection bag and donor.

Additional objects, features and advantages will be apparent in the written description which follows.

SUMMARY OF THE INVENTION

In one aspect of the method of the invention, a quantity of the donor's whole blood is first collected in a blood collection container, the whole blood being comprised of plasma and red blood cells. A key is associated with the collection container, the key being unique to the donor. A flow control means is installed at some point in the return flow line used to return red blood cells to the donor. The flow control means preferably includes a lock which is adapted to receive the unique key. The whole blood is separated in the blood collection container into plasma and red cells. The plasma is removed from the blood collection container and connected to the return flow line. The flow control means is then unlocked with the unique key and the donor is reinfused with red blood cells.

In another aspect of the method of the invention, the blood collection container is preferably provided with a collecting port, a plasma removal port and a reinfusion port. Preferably, the reinfusion port is sealed with a seal means bearing identifying indicia, the identifying indicia being unique to the donor. The seal means are removed from the reinfusion port only after verifying the identifying indicia with the correct donor.

The apparatus making up the flow control means preferably includes a roller clamp in the return flow line which is initially positioned to restrict flow through the return flow line. The roller clamp is received within a lock box mounted on an I.V. pole in the vicinity of the donor. The lock box is provided with a swing arm movable by means of the unique key between a locked position in which the roller clamp is secured within the lock box and an unlocked position. After removing the plasma from the blood collection container and reinstalling the container within the blood return system, the lock box can be unlocked with the unique key and the position of the roller clamp can be changed to allow flow through the return flow line. The donor can then be reinfused with red blood cells.

BRIEF DESCRIPTION OF THE DRAWINGS

FIG. 1 is a perspective view of an I.V. pole having the lock box of the invention installed thereon.

FIG. 2 is a perspective view of the unique key used with the lock box of FIG. 1.

FIG. 3 is a view of the key similar to FIG. 2 but with portions broken away.

DETAILED DESCRIPTION OF THE INVENTION

Figure 4:
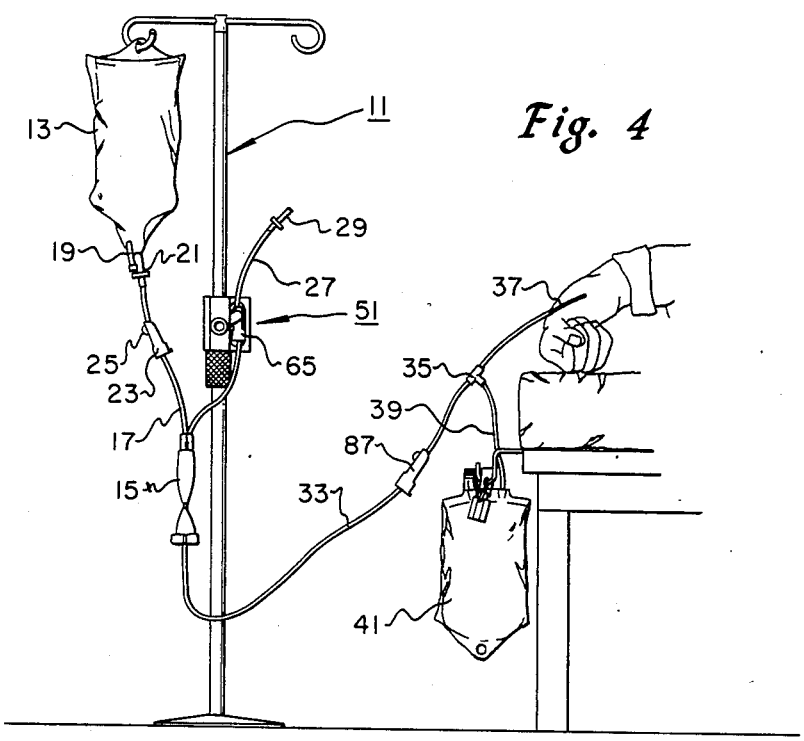
FIG. 4 is a simplified schematic of a plasmapheresis flow assembly showing the collection of whole blood into a blood collection container.

FIG. 4 shows a plasmapheresis assembly which includes the safety apparatus used in practicing the method of the invention. The plasmapheresis assembly shown in FIG. 4 includes an I.V. pole 11 from which is suspended a saline container 13. The saline container is connected to a filter drip chamber 15 by a length of flexible conduit 17. The conduit 17 has resiliently deformably sidewalls which can be pinched or crimped together in response to an external force, thereby closing the fluid path through the conduit or tubing. The conduit is also capable of resiliently returning to a normally open position when the external force is removed. The saline container 13 and conduit 17 can be manufactured from plastic transparent material of medical grade quality, such as polyethylene, vinyl, plastic, or polyvinyl chloride. The saline container 13 has one or more outlet ports 19, one of which is connected to the flexible conduit 17 by means of a spiked end portion 21. A conventional roller clamp 23 is present on the flexible conduit between the saline container 13 and the filter drip chamber 15 for selectively opening and closing off flow through the conduit. This is accomplished by positioning the roller 25 which is carried in a guideway of the roller clamp and will be familiar to those skilled in the art.

The filter drip chamber 15 forms a "Y" between the flexible conduit 17 and an identical length of conduit 27. Conduit 27 is also provided with a spiked end portion 29 and with a roller clamp 31. A length of primary conduit 33 passes from the bottom of the filter drip chamber 15 through a manifold 35 to an intravenous needle 37 of the type which is commercially available. The manifold 35 is connected by a length of auxiliary conduit 39 to an inlet port of a whole blood collection container 41.

Figure 6:
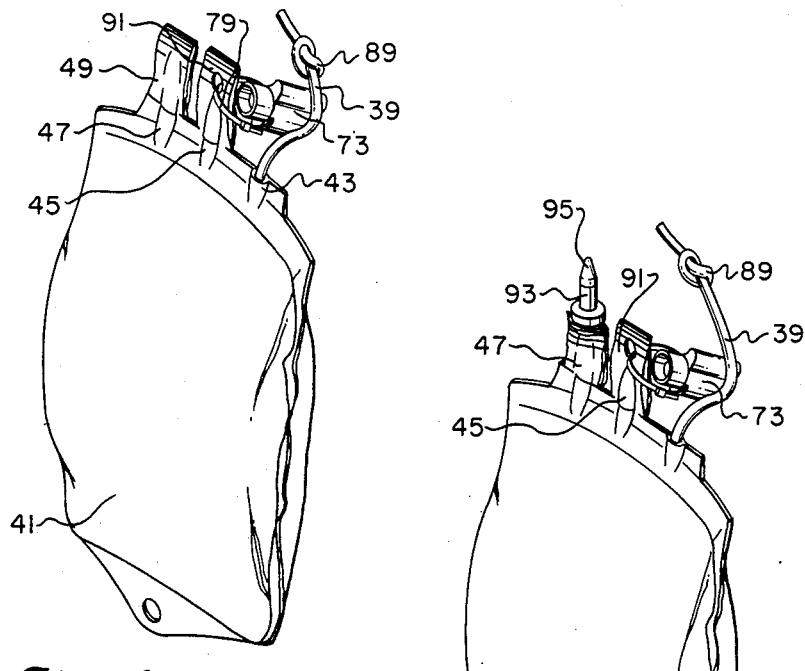
FIG. 6 is a perspective view of the blood collection container prior to centrifuging.

As best seen in FIG. 6, the whole blood collection container 41 includes the collection port 43, a reinfusion port 45 and a plasma removal port 47. The container 41 can be fabricated from a plastic material, similar to the material of conduit 17. The reinfusion port 45 and plasma removal port 47 are provided with a normally closed membrane 49 which must be separated prior to the insertion of a spiked end portion 21 into the port.

As shown in FIG. 1, the apparatus used in the method of the invention includes a lock box (designated generally as 51 in FIG. 1) for rendering the return blood flow assembly inoperative until identifying indicia on the blood collection container have been matched with the correct donor. The lock box 51 includes a metal housing 53 having an arcuate recess 55 formed therein for receiving the vertical leg 57 of the I.V. pole. A side wall 59 of the lock box 51 closes off the recess 55 after installation on the vertical leg 57 so that the lock box surrounds the vertical leg 57. A collar 61 on the vertical leg 57 prevents the lock box 51 from being lowered below the normal installation position. The lock box can also be provided with positioning means such as tap screws (not shown) which pass through the side walls of the box and contact or penetrate the vertical leg 57 to prevent removal of the lock box and to maintain the lock box at a particular desired vertical location.

The lock box 51 is provided with a longitudinal opening 63 which runs generally parallel to the vertical leg 57 and which is adapted to receive a conventional roller clamp 65 (FIG. 4). Access to the longitudinal opening 63 is governed by the position of a swing arm 67 of a tubular lock 69. The tubular lock is similar to those found in airport lockers and can be purchased from Chicago Lock Company, 4311 West Bellmont Avenue, Chicago, Ill., as the Model 4153.

The tubular lock 69 includes a key opening 71 for receiving a conventional key 73 (FIG. 3). The key 73 cannot normally be removed from the key opening 71 unless the swing arm 67 is moved from the open position shown in FIG. 1 to the closed position shown in FIG. 4.

The key 73 has a transverse opening 75 provided in the tubular barrel portion 77 for receiving a connecting strap, such as tie 79. With the tie 79 inserted through the transverse opening 75, the key cannot be used to open the tubular lock 69.

As shown in FIG. 2, the metal key 73 is encapsulated by a protective coating 81. This can be any suitable rubber-like material and includes a cylindrical opening 83 for providing access to the tubular barrel portion 77. The coating 81 is also provided with openings 85 in alignment with the transverse opening 75 of the key.

In the method of the invention, the plasmapheresis assembly is arranged as shown in simplified fashion in FIG. 4. The roller clamp 65 in the return flow conduit 27 is in the closed position so that fluid cannot pass from the spiked end portion 29 in the direction of the filter drip chamber 15. The swing arm 67 of the lock box 51 is in the closed position, thereby preventing access to the roller clamp. After the venipuncture is made, blood is directed from the donor through manifold 35 and auxiliary tubing 39 into the inlet port of the whole blood collection container 41. Flow through the primary conduit 33 can be controlled by the roller clamp 87. After a unit of whole blood has been collected in the container 41, the auxiliary tubing 39 is typically sealed closed. This can be accomplished in any number of known ways such as the use of spaced-apart hand seal clips, or by the formation of a hermetic, snap-apart seal. The sealing off operation is illustrated in FIG. 6 by the knot 89 in the auxiliary tubing 39. At this stage, the container 41 has been severed from the remaining assembly.

It will also be noted that the reinfusion port 45 of the container 41 is sealed by means of the tie 79 which passes through an opening in the membrane 91. The tie 79 passes through the transverse opening (75 in FIG. 3) of the unique key 73. Port 47 is thus the only available port for removing plasma from the container 41 without violating sterile procedures.

The container 41 is then taken to the centrifuge station (not shown) where the whole blood is separated into plasma and red cells. The centrifuge operating personnel are instructed to perform the centrifuge operation only in the event that a unique key or other sealing device associated with the correct donor is in place as shown in FIG. 6.

Figure 5:
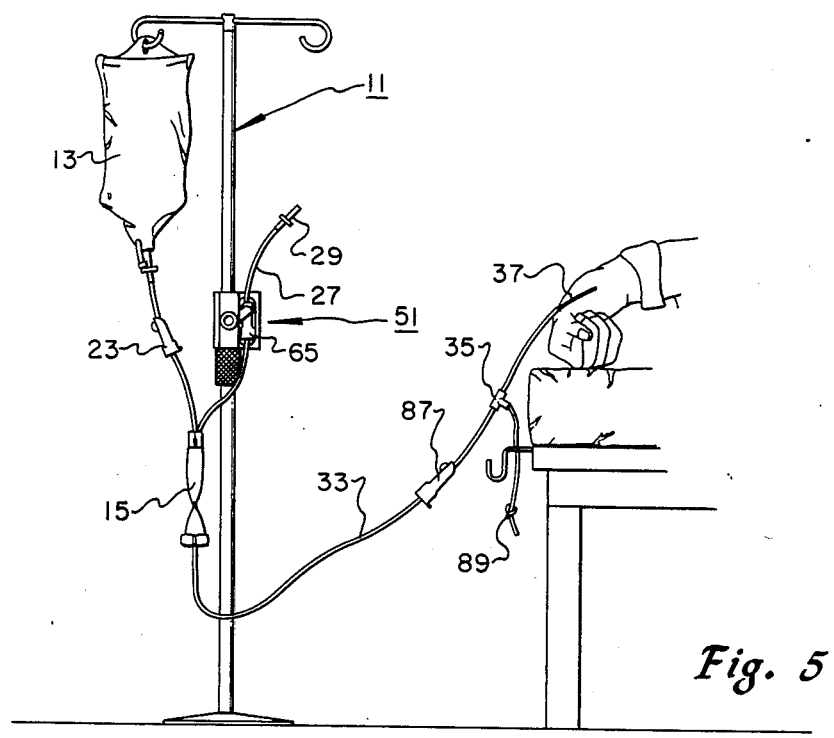
FIG. 5 is a schematic view similar to FIG. 4 with the blood collection container removed to the centrifuge operation.
Figure 7:
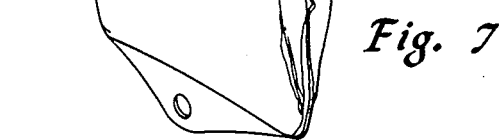
FIG. 7 is a perspective view similar to FIG. 6 showing the blood collection container after completion of the centrifuge operation.

The plasma is expressed from the container 41 by known manual or automatic means and collected for fractionation, leving the red cells in the container 41. At the conclusion of the centrifuge operation, the container 41 appears as in FIG. 7 with a spike 93 inserted within the plasma removal port 47. The spike 93 is sealed at end region 95. During the centrifuge operation, the plasmapheresis assembly remains in the condition illustrated in FIG. 5.

Figure 8:
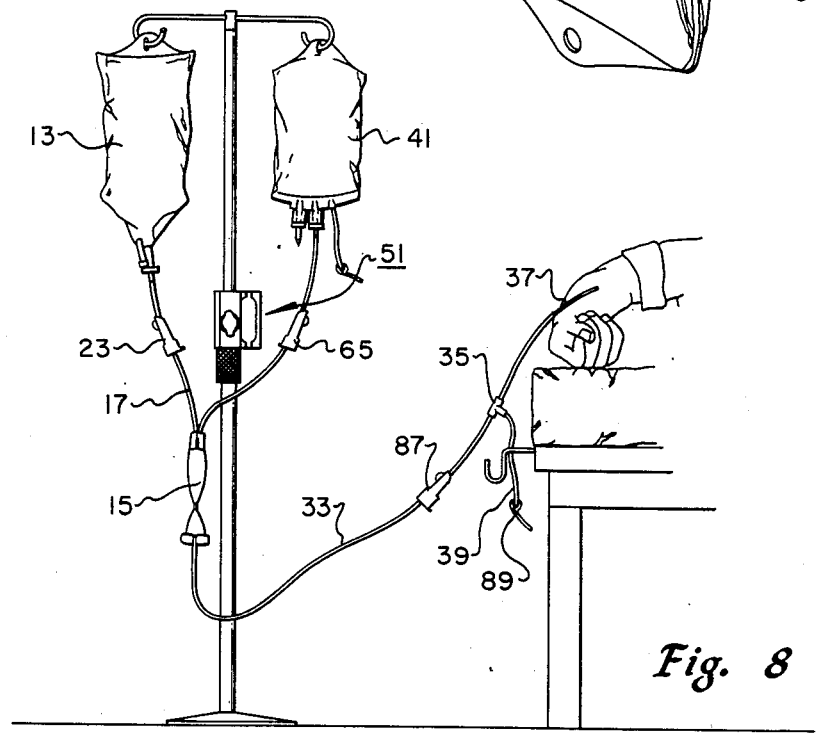
FIG. 8 is a schematic view similar to FIG. 4 showing the reinfusion of the donor with red blood cells.

At the conclusion of the centrifuge operation, the container 41 is hung from the I.V. pole 11 and the key strap and key are removed from the reinfusion port 45, allowing the membrane 91 to be opened for the insertion of the spiked end portion 29 of the return blood flow line 27. At this point, the assembly is still inoperative, since flow from container 41 cannot pass through the roller clamp 65 which is contained within the lock box 51. The assembly can only be rendered operative by matching the correct unique key 73 to the lock box 53, whereby the swing arm 67 can be moved to the open position to allow removal of the roller clamp 65, as shown in FIG. 8.

During the time the whole blood in the container 41 is being processed, flow of saline can be induced from the container 13 through the filter drip chamber 15 and through the primary tubing to flush traces of blood from the flow paths and to maintain the patency of the needle 37. This can be accomplished by opening the roller clamps 23 and 87.

Although the preferred flow control method includes the step of locking the roller clamp 35 within the lock box 51, it will be understood that other portions of the assembly can be locked in an inoperative position. For instance, the spiked end portion 29 is adapted to be received within the longitudinal opening 63 of the lock box 51 and can be locked during the centrifuge operation. The lock box 53 can also be provided with a compressive member, as a part of the swimg arm 67, which would be used to compress a selected portion of the flexible conduit passing within the longitudinal opening 63. In this way, flow would be closed off through the tubing until the lock box was again opened with the unique key to remove the force exerted by the compressive member upon the flexible conduit.

An invention has been provided with several advantages. The plasmapheresis assembly insures safety in matching the returning red blood cells to the correct donor by rendering the device inoperative until identifying indicia have been verified. Rather than relying upon printed indicia or color matching, the present system utilizes a unique key which is received within a lock box. By associating the lock box with the donor and the key with the blood collection bag, mistakes in matching bags and donors can be eliminated. By encapsulating the unique key in a protective coating, any danger of puncturing the collection bag is eliminated. The lock box assembly is easily visible to supervisory personnel, so that any violation of the established operating procedures would be immediately apparent.

While the invention has been shown in only one of its forms, it is not thus limited but is susceptible to various changes and modifications without departing from the spirit thereof.

I claim:

1. A method for avoiding mistakes in returning red blood cells to the correct donor during plasmapheresis, the method comprising the steps of:
    collecting a quantity of the donor's whole blood in a whole blood collection container, the whole blood collection container being provided with a collecting port, a plasma removal port and a reinfusion port, and wherein the reinfusion port is sealed with a seal means bearing identifying indicia, the identifying indicia being unique to the donor;
    separating the whole blood in the blood collection container into plasma and red cells;
    removing the plasma from the blood collection container through the plasma removal port and sealing the plasma removal port;
    removing the seal means from the reinfusion port after verifying the identifying indicia with the correct donor;
    reinfusing the donor with the red cells; and
    wherein the identifying indica comprise a key and lock.

2. The method of claim 1, wherein the key is attached to the reinfusion port as a part of the seal means.

3. The method of claim 2, wherein the key is encapsulated in a protective coating, and wherein the key and protective coating are provided with a transverse opening, the key being attached to the reinfusion port by means of a tie strap which passes through the transverse opening.

4. A method for avoiding mistakes in returning red blood cells to the correct donor during plasmapheresis, the method comprising the steps of:
    collecting a quantity of the donor's whole blood in a whole blood collection container, the whole blood collection container being provided with a collecting port, a plasma removal port and a reinfusion port, and wherein the reinfusion port is sealed with a seal means including a key which is unique to the donor;
    installing flow control means at some point in the return flow line used to return red blood cells to the donor, the flow control means including a lock adapted to receive the unique key;
    separating the whole blood in the blood collection container into plasma and red cells;
    removing the plasma from the blood collection container through the plasma removal port and sealing the plasma removal port;
    removing the seal means from the reinfusion port and connecting the return flow line to the reinfusion port;
    unlocking the flow control means with the key; and
    reinfusing the donor with the red cells.

5. The method of claim 4, wherein the flow control means includes a roller clamp in the return flow line, the roller clamp being received within lock box which is opened and closed by means of the unique key.

6. The method of claim 4, wherein the flow control means is a spiked end portion of the return flow line which is received within a lock box, the lock box being opened and closed by means of the unique key.

7. The method of claim 4, wherein the flow control means is a constricted region in the return flow line which is received within a lock box, the lock box being opened and closed by means of the unique key.

8. A method for avoiding mistakes in returning red blood cells to the correct donor during plasmapheresis, the method comprising the steps of:
    collecting a quantity of the donor's whole blood in a whole blood collection container, the whole blood collection container being provided with a collecting port, a plasma removal port and a reinfusion port, and wherein the reinfusion port is sealed with a seal means including a key which is unique to the donor;
    installing flow control means at some point in the return flow line used to return red blood cells to the donor, the flow control means including a roller clamp in the return flow line which is initially positioned to restrict flow through the return flow line, the roller clamp being received within a lock box mounted on an I.V. pole in the vicinity of the donor, and the lock box being provided with a swing arm movable by means of the unique key between a locked position in which the roller clamp is secured within the lock box and an unlocked position;
    separating the whole blood in the blood collection container into plasma and red cells;
    removing the plasma from the blood collection container through the plasma removal port and sealing the plasma removal port;
    removing the seal means from the reinfusion port and connecting the return flow line to the reinfusion port;
    unlocking the lock box with the key;
    changing the position of the roller clamp to allow flow through the return flow line; and
    reinfusing the donor with the red cells.

9. A method for avoiding mistakes in returning red blood cells to the correct donor during plasmapheresis, the method comprising the steps of:
    collecting a quantity of the donor's whole blood in a whole blood collection container, the whole blood being comprised of plasma and red blood cells;
    associating a key with the collection container, the key being unique to the donor;
    installing flow control means at some point in the return flow line used to return red blood cells to the donor, the flow control means including a lock adapted to receive the unique key;
    separating the whole blood in the blood collection container into plasma and red cells;

removing the plasma from the blood collection container and connecting the return flow line to the container;

unlocking the flow control means with the key; and reinfusing the donor with the red blood cells.

10. The method of claim 9, wherein the key is attached to the whole blood collection container prior to separating the whole blood into plasma and red blood cells.

11. The method of claim 10, wherein the blood collection container is provided with a reinfusion port and wherein the key is attached to the collecting container by a strap which also seals the reinfusion port.

12. An apparatus used to avoid mistakes in returning red blood cells to the correct donor during plasmapheresis, comprising:

a stand for supporting a blood collection container containing red blood cells to be returned to the donor;

a return blood flow line for connecting the blood collection container to the donor;

flow restricting means located at some point in the return blood flow line for temporarily interrupting the flow of fluid through the return blood flow line; and a lock box installed on the stand, the lock box having an opening for receiving the flow restricting means and having a key operated lock movable by means of a unique key between a locked position denying access to the flow restricting means and an unlocked position.

13. The apparatus of claim 12, wherein the flow restricting means is a roller clamp.

* * * * *